(12) United States Patent
Schulz et al.

(10) Patent No.: US 8,080,010 B2
(45) Date of Patent: Dec. 20, 2011

(54) DEVICE AND TEMPLATE FOR CANINE HUMERAL SLIDE OSTEOTOMY

(75) Inventors: Kurt S. Schulz, Hollis, NH (US); Michael O. Khowaylo, Mahwah, NJ (US); Patrick M. White, West Chester, PA (US); Robert A. Young, Loganville, GA (US)

(73) Assignees: Greatbatch Medical S.A., Orvin (CH); New Generation Devices, Inc., Glen Rock, NJ (US)

( * ) Notice: Subject to any disclaimer, the term of this patent is extended or adjusted under 35 U.S.C. 154(b) by 1037 days.

(21) Appl. No.: 11/552,585

(22) Filed: Oct. 25, 2006

(65) Prior Publication Data

US 2008/0039851 A1 Feb. 14, 2008

Related U.S. Application Data

(63) Continuation of application No. PCT/US2006/006620, filed on Feb. 23, 2006, and a continuation-in-part of application No. 10/809,034, filed on Mar. 25, 2004, now Pat. No. 7,722,653.

(60) Provisional application No. 60/730,462, filed on Oct. 25, 2005.

(51) Int. Cl.
*A61B 17/80* (2006.01)
*A61B 17/66* (2006.01)
*A61B 17/56* (2006.01)

(52) U.S. Cl. ............... 606/70; 606/280; 606/282

(58) Field of Classification Search .......... 606/70, 606/71, 86, 87–89, 280–299
See application file for complete search history.

(56) References Cited

U.S. PATENT DOCUMENTS

| 2,486,303 | A | * | 10/1949 | Longfellow | 606/71 |
|-----------|---|---|---------|------------|--------|
| 2,699,774 | A | | 1/1955 | Livingston | |
| 3,552,389 | A | | 1/1971 | Allgover et al. | |
| 3,659,595 | A | | 5/1972 | Haboush | |
| 3,716,050 | A | | 2/1973 | Johnston | |
| 3,779,240 | A | * | 12/1973 | Kondo | 606/282 |

(Continued)

FOREIGN PATENT DOCUMENTS

DE    02 07 884    3/1909

(Continued)

OTHER PUBLICATIONS

Brueckmann et al., Proximal Tibial Osteotomy, Orthopedic Clinics of North America, vol. 13, No. 1, (Jan. 1982), p. 3-16.

(Continued)

*Primary Examiner* — Thomas C. Barrett
*Assistant Examiner* — Matthew Lawson
(74) *Attorney, Agent, or Firm* — Michael F. Scalise

(57) ABSTRACT

In the field of canine humeral osteotomy, an osteotomy plate including a proximal plate portion lying substantially in a first plane for application to the humerus. The proximal plate portion has a bottom surface adapted for application to the surface of the humerus, and the proximal plate portion has at least one overlapping hole formed therein. The osteotomy plate also includes a distal plate portion lying substantially in a second plane for application to the humerus. The distal plate portion has a bottom surface adapted for application to the surface of the humerus, and the distal plate portion has at least one overlapping hole formed therein. The osteotomy plate also includes a transition region connecting the proximal plate portion to the distal plate portion.

20 Claims, 5 Drawing Sheets

U.S. PATENT DOCUMENTS

| | | | |
|---|---|---|---|
| 3,824,995 A | | 7/1974 | Getscher et al. |
| 3,842,825 A | | 10/1974 | Wagner |
| RE28,841 E | | 6/1976 | Allgower et al. |
| 4,120,298 A | | 10/1978 | Fixel |
| 4,219,015 A | * | 8/1980 | Steinemann ............... 606/280 |
| 4,297,993 A | | 11/1981 | Harle |
| 4,403,606 A | | 9/1983 | Woo et al. |
| 4,408,601 A | * | 10/1983 | Wenk ............................ 606/282 |
| 4,409,973 A | | 10/1983 | Neufeld |
| 4,421,112 A | | 12/1983 | Mains et al. |
| 4,454,876 A | | 6/1984 | Mears |
| RE31,628 E | | 7/1984 | Allgower et al. |
| 4,493,317 A | | 1/1985 | Klaue |
| 4,498,601 A | | 2/1985 | Fort |
| 4,501,268 A | | 2/1985 | Comparetto |
| 4,502,474 A | | 3/1985 | Comparetto |
| 4,503,848 A | | 3/1985 | Caspar et al. |
| 4,509,511 A | | 4/1985 | Neufeld |
| 4,513,744 A | | 4/1985 | Klaue |
| 4,524,765 A | | 6/1985 | de Zbikowski |
| 4,545,876 A | | 10/1985 | McGivern, Jr. |
| 4,565,191 A | | 1/1986 | Slocum |
| 4,565,193 A | | 1/1986 | Streli |
| 4,611,581 A | | 9/1986 | Steffee |
| 4,662,891 A | | 5/1987 | Noiles |
| 4,677,973 A | | 7/1987 | Slocum |
| 4,696,290 A | | 9/1987 | Steffee |
| 4,762,122 A | | 8/1988 | Slocum |
| 4,790,297 A | | 12/1988 | Luque |
| 4,794,918 A | | 1/1989 | Wolter |
| 4,800,874 A | | 1/1989 | David et al. |
| 4,838,252 A | | 6/1989 | Klaue |
| 4,867,144 A | | 9/1989 | Karas et al. |
| 4,875,475 A | | 10/1989 | Comte et al. |
| 4,887,595 A | | 12/1989 | Heinig et al. |
| 4,957,479 A | | 9/1990 | Roemer |
| 4,957,496 A | | 9/1990 | Schmidt |
| 4,957,497 A | | 9/1990 | Hoogland et al. |
| 4,959,065 A | | 9/1990 | Arnett et al. |
| 4,988,350 A | | 1/1991 | Herzberg |
| 5,002,544 A | | 3/1991 | Klaue et al. |
| 5,006,120 A | | 4/1991 | Carter |
| 5,015,248 A | | 5/1991 | Burstein et al. |
| 5,041,113 A | * | 8/1991 | Biedermann et al. ......... 606/288 |
| 5,042,983 A | * | 8/1991 | Rayhack ........................ 606/87 |
| 5,085,660 A | | 2/1992 | Lin |
| 5,087,260 A | | 2/1992 | Fixel |
| 5,209,751 A | | 5/1993 | Farris et al. |
| 5,216,941 A | | 6/1993 | Kolvereid |
| 5,232,249 A | | 8/1993 | Kolvereid |
| 5,261,910 A | | 11/1993 | Warden et al. |
| 5,275,601 A | | 1/1994 | Gogolewski et al. |
| 5,304,180 A | | 4/1994 | Slocum |
| 5,324,290 A | | 6/1994 | Zdeblick et al. |
| 5,364,399 A | | 11/1994 | Lowery et al. |
| 5,429,641 A | * | 7/1995 | Gotfried ........................ 606/67 |
| 5,487,741 A | * | 1/1996 | Maruyama et al. ........... 606/60 |
| 5,601,553 A | | 2/1997 | Trebing et al. |
| 5,681,311 A | | 10/1997 | Foley et al. |
| 5,709,686 A | * | 1/1998 | Talos et al. ................... 606/281 |
| 5,733,287 A | | 3/1998 | Tepic et al. |
| 5,741,258 A | | 4/1998 | Klaue et al. |
| 5,810,823 A | | 9/1998 | Klaue et al. |
| 5,851,207 A | | 12/1998 | Cesarone |
| 5,904,684 A | * | 5/1999 | Rooks ........................ 606/86 B |
| 5,921,988 A | * | 7/1999 | Legrand ........................ 606/87 |
| 5,968,047 A | | 10/1999 | Reed |
| 5,976,141 A | | 11/1999 | Haag et al. |
| 5,997,541 A | | 12/1999 | Schenk |
| 6,048,344 A | | 4/2000 | Schenk |
| 6,096,060 A | | 8/2000 | Fitts et al. |
| 6,183,475 B1 | * | 2/2001 | Lester et al. ................. 606/281 |
| 6,206,881 B1 | | 3/2001 | Frigg et al. |
| 6,309,393 B1 | | 10/2001 | Tepic et al. |
| 6,331,179 B1 | | 12/2001 | Freid et al. |
| 6,358,250 B1 | | 3/2002 | Orbay |
| 6,406,478 B1 | | 6/2002 | Kuo |
| 6,533,786 B1 | * | 3/2003 | Needham et al. ............. 606/282 |
| 6,605,090 B1 | * | 8/2003 | Trieu et al. .................... 606/281 |
| 6,623,486 B1 | | 9/2003 | Weaver et al. |
| 6,669,701 B2 | | 12/2003 | Steiner et al. |
| 6,719,759 B2 | * | 4/2004 | Wagner et al. ................ 606/282 |
| 6,767,351 B2 | | 7/2004 | Orbay et al. |
| 6,821,278 B2 | | 11/2004 | Frigg et al. |
| 7,008,427 B2 | * | 3/2006 | Sevrain ........................... 606/71 |
| 7,048,739 B2 | | 5/2006 | Konieczynski |
| 7,063,701 B2 | | 6/2006 | Michelson |
| 7,090,676 B2 | | 8/2006 | Huebner et al. |
| 7,354,441 B2 | * | 4/2008 | Frigg ............................ 606/261 |
| 2002/0045901 A1 | | 4/2002 | Wagner et al. |
| 2002/0156474 A1 | | 10/2002 | Wack et al. |
| 2002/0183752 A1 | | 12/2002 | Steiner et al. |
| 2003/0040748 A1 | | 2/2003 | Aikins et al. |
| 2004/0026029 A1 | | 2/2004 | Martin et al. |
| 2004/0167522 A1 | * | 8/2004 | Niederberger et al. ......... 606/69 |
| 2004/0181228 A1 | | 9/2004 | Wagner et al. |
| 2004/0193164 A1 | | 9/2004 | Orbay |
| 2004/0193165 A1 | | 9/2004 | Orbay |
| 2005/0010226 A1 | * | 1/2005 | Grady et al. ..................... 606/69 |
| 2005/0049594 A1 | * | 3/2005 | Wack et al. ..................... 606/69 |
| 2005/0065524 A1 | * | 3/2005 | Orbay ............................. 606/69 |
| 2005/0080421 A1 | * | 4/2005 | Weaver et al. .................. 606/69 |
| 2005/0216008 A1 | | 9/2005 | Zwirnmann et al. |
| 2005/0216009 A1 | | 9/2005 | Michelson |
| 2005/0245931 A1 | | 11/2005 | Orbay |
| 2005/0251138 A1 | * | 11/2005 | Boris et al. ....................... 606/61 |
| 2006/0009771 A1 | | 1/2006 | Orbay et al. |
| 2006/0212035 A1 | | 9/2006 | Wotton, III |

FOREIGN PATENT DOCUMENTS

| | | |
|---|---|---|
| DE | 2340880 A1 | 4/1975 |
| DE | 28 06 414 | 10/1978 |
| DE | 43 41 980 | 6/1995 |
| DE | 43 43 117 | 6/1995 |
| EP | 0 100 114 | 2/1984 |
| EP | 0 355 035 | 2/1990 |
| FR | 2 472 373 | 7/1981 |
| FR | 2480106 | 10/1981 |
| FR | 2 556 583 | 6/1985 |
| FR | 2 606 268 | 5/1988 |
| FR | 2674118 | 9/1992 |
| WO | WO 00/53110 | 9/2000 |
| WO | WO 00/53111 | 9/2000 |
| WO | WO 01/19267 | 3/2001 |
| WO | WO 01/54601 | 8/2001 |
| WO | WO 01/57834 | 8/2001 |
| WO | WO 02/00127 | 1/2002 |
| WO | WO 02/096309 | 12/2002 |
| WO | WO 2004/084701 | 10/2004 |
| WO | WO 2004/089233 | 10/2004 |
| WO | 2005032386 A1 | 4/2005 |
| WO | 2005041796 A1 | 5/2005 |
| WO | WO2005/117732 | 12/2005 |
| WO | 2006014391 A1 | 2/2006 |

OTHER PUBLICATIONS

Sundaram et al., Dome Osteotomy of the Tibia for Osteoarthritis of the Knee, The Journal of Bone and Joint Surgery, vol. 68-B, No. 5, (Nov. 1986), p. 782-786.

Slocum et al, Tibial Plateau Leveling Osteotomy for Repair of Cranial Cruciate Ligament Rupture in the Canine, Veterinary Clinics of North America: Small Animal Practice, vol. 23, No. 4, (Jul. 1993), p. 777-795.

Reif et al, Effect of Tibial Plateau Leveling on Stability of the Canine Cranial Cruciate-Deficient Stifle Joint: An In Vitro Study, Veterinary Surgery, 31, (2002), p. 147-154.

Wheeler et al., In Vitro Effects of Osteotomy Angle and Osteotomy Reduction on Tibial Angulation and Rotation During the Tibial Plateau-Leveling Osteotomy Procedure, Veterinary Surgery, 32, (2003), p. 371-377.

Fettig et al., Observer Variability of Tibial Plateau Slope Measurement in 40 Dogs With Cranial Cruciate Ligament-Deficient Stifle Joints, Veterinary Surgery, 32, (2003), p. 471-478.

Miniaci et al., Proximal Tibial Osteotomy. A New Fixation Device, PubMed Article.

Lang et al., Cylindrical Osteotomy of the Upper End of the Tibia, PubMed Article.

Schneider et al., Cylindrical Osteotomy of the Upper Extremity of the Tibia with Advancement of the Patellar Ligament. Biomechanical Treatment of Gonarthrosis, PubMed Article.

Cassarino et al., High Domed Tibial Osteotomy in the Treatment of Angular Deviations of the Knee. A New System of Surgical Instrumentation, PubMed Article.

Soccetti et al., Domed High Tibial Osteotomy: the Long-Term Results in Tibiofemoral Arthritis with and without Malalignment of the Extensor Apparatus, PubMed Article.

Slocum et al., Current Techniques in Small Animal Surgery, Baltimore: Williams & Wilkins, TX-4-606-643, (1997), 1340 pages.

Slocum et al., Dog Trot, VAu-91-980, (1985).

Sundaram et al., Dome osteotomy of the tibia for osteoarthritis of the knee, PubMed Article.

Boulay JP, Fragmented medial coronoid process of the ulna in the dog, Vet Clin North Am Small Anim Pract, 1998, p. 51-74, vol. 28, No. 1.

Cook J, Forelimb lameness in the young patient, Vet Clin North Am Small Anim Pract, 2001, p. 55-83, vol. 31, No. 1.

Ness MG, Treatment of fragmented coronoid process in young dogs by proximal ulnar osteotomy, J Small Anim Pract, 1998, p. 15-18, vol. 39, No. 1.

Lewis, Evaluation of shelf arthroplasty as a treatment for hip dysplasia in dogs, J Am Vet Med Assoc, 1996, p. 1838-45, vol. 208, No. 11.

Read 1990.

Bouck 1995.

Meyer-Lindenberg 2003 VCO1.

Conz 1998/2001.

Decamp 1993.

UCDavis School of Veterinary Medicine. Pressure, Arthritis, and the Canine Elbow.

\* cited by examiner

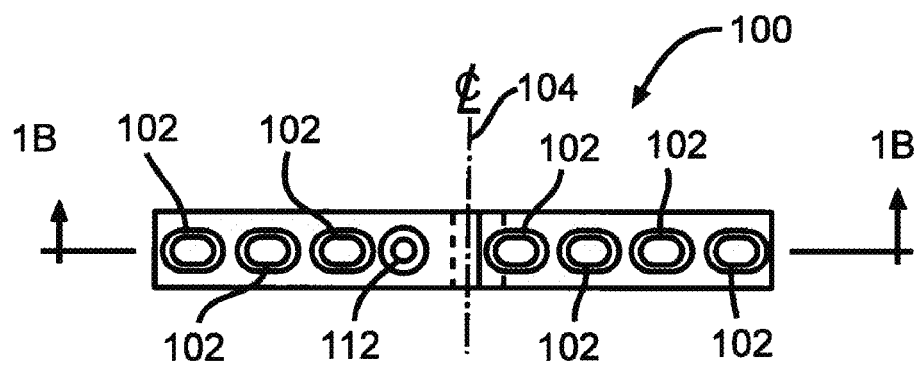
FIG. 1A
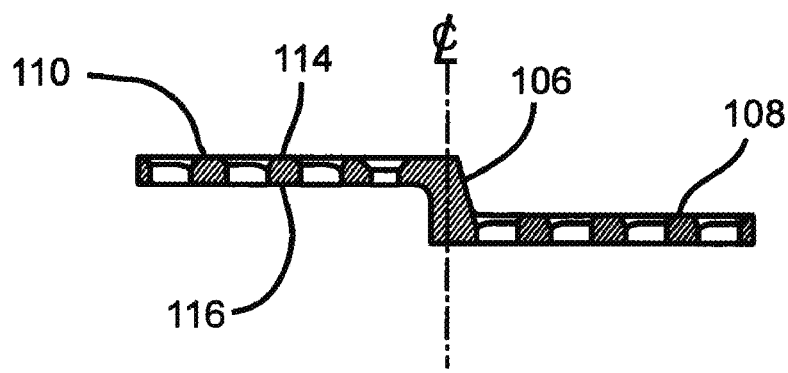
FIG. 1B
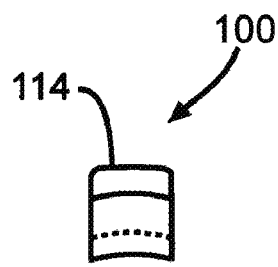 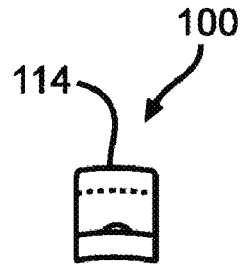
FIG. 1C     FIG. 1D

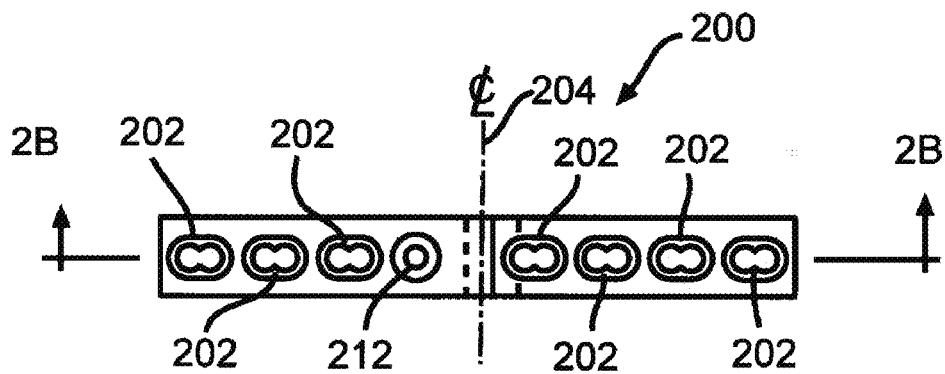
FIG. 2A
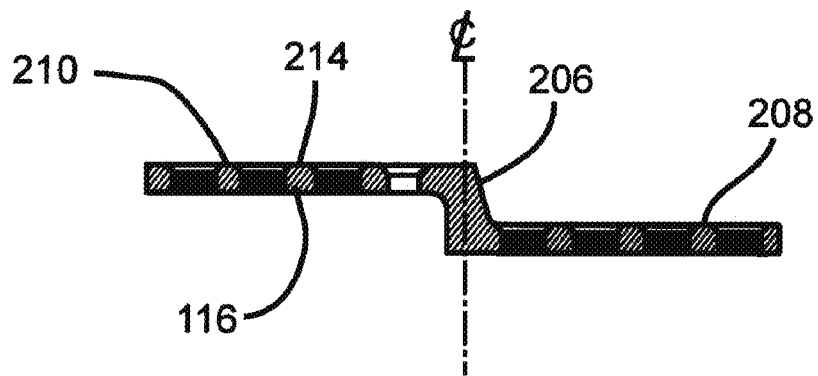
FIG. 2B
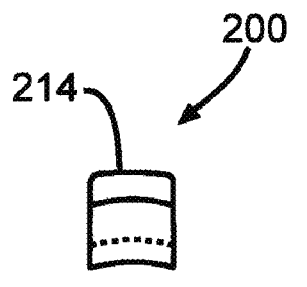 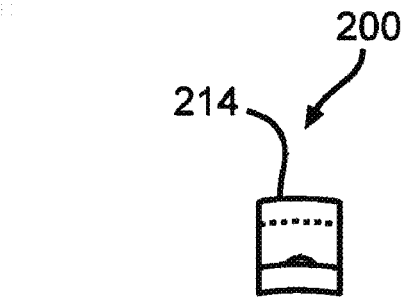
FIG. 2C  FIG. 2D

DEVICE AND TEMPLATE FOR CANINE HUMERAL SLIDE OSTEOTOMY

CROSS-REFERENCES TO RELATED APPLICATIONS

The present application claims priority to U.S. Provisional Application Ser. No. 60/730,462, filed Oct. 25, 2005, which is herein incorporated by reference in its entirety for all purposes. The present application is a continuation of International Patent Application No. PCT/US2006/006620, filed Feb. 23, 2006 and a continuation-in-part application of U.S. application Ser. No. 10/809,034 now U.S. Pat. No. 7,722,653, filed Mar. 25, 2004, the disclosures of which are herein incorporated by reference in their entireties for all purposes, not inconsistent with the present application.

BACKGROUND OF THE INVENTION

The present invention is directed to a bone plating system, and in particular to a system for the fixation of a canine humerus following a slide osteotomy.

Elbow dysplasia, including fragmentation of the medial coronoid process of the ulna (FCP), is the most common forelimb orthopedic disorder recognized to cause joint pain and lameness in large and giant breed dogs. Fragmented medial coronoid process ("FCP") with secondary osteoarthritis is one of the most common, yet poorly understood, hereditary syndromes of pure and mixed breed dogs. FCP is characterized by fragmentation of the cartilage and subchondral bone on the lateral aspect of the medial coronoid process, with grade II to grade IV cartilage erosion over the center of the medial coronoid process. The pathophysiology of FCP has not been well defined but may include joint incongruity and increased transarticular pressure.

Management of FCP consists of surgical and medical treatments. Surgical management includes removal of fragments and debridement of cartilage lesions, proximal ulnar osteotomy, and total elbow arthroplasty. Studies have historically suggested that when compared with medical treatment, surgical removal of FCP via arthrotomy did not result in improved long-term clinical outcome (e.g., see, Read 1990, Bouck 1995, Boulay 1998, Cook 2001). This finding was recently challenged, however, in a study where 247 elbow joints were treated with a conventional arthrotomy and 271 joints were treated by arthroscopy. It was reported that arthroscopy provided better functional results, but that progression of artbrosis was similar following both techniques (e.g., see, Meyer-Lindenberg 2003 VC01).

The purposes of proximal ulnar osteotomy are to alter the biomechanical forces in the elbow joint by redistributing articular loads to alleviate excessive loads on the coronoid process of the ulna. Little is known about the effectiveness of this procedure, with no long term follow up or placebo control studies (e.g., see, Ness 1998). Total elbow arthroplasty ("TEA") has been reported to achieve success for severe elbow osteoarthritis, but the success in cases with mild to moderate elbow arthritis has yet to be determined (e.g., see, Lewis 1996, Conz 1998, 2001).

Ulnar osteotomies have been used to correct or alter loads across the canine elbow joint for the management of FCP with the goal of correcting radio-ulnar incongruity (e.g., see, Ness 1998). These techniques presume that the proximal ulnar articular surface is elevated above the radial articular surface leading to increased medial compartmental pressure, cartilage degeneration and subchondral bone fragmentation. A joint surface contact study simulating radio-ulnar incongruence did demonstrate that radio-ulnar incongruence results in shifting of contact to the lateral region of the medial coronoid process, the area where fragmentation most often occurs (e.g., see, DeCamp 1993). The study also evaluated the effect of proximal and distal ulnar osteotomies on correction of the incongruity. A proximal ulnar osteotomy stabilized with an intramedullary pin did restore normal contact patterns in the in vitro model; however, radio-ulnar incongruence has not been definitively identified as the cause of FCP. In the absence of this incongruence, an osteotomy of the ulna may lead to varus deformity of the limb and subsequently increased loads on the medial compartment.

Thus, there exists a need for an improved treatment of the canine elbow joint, as well as a related bone plating system for this improved treatment.

BRIEF SUMMARY OF THE INVENTION

The present invention is directed in general to the field of canine humeral osteotomy, and in particular to an osteotomy plate. In one embodiment, the osteotomy plate includes a proximal plate portion lying substantially in a first plane for application to the humerus. The proximal plate portion has a bottom surface adapted for application to the surface of the humerus, and the proximal plate portion has at least one overlapping hole formed therein. The osteotomy plate also includes a distal plate portion lying substantially in a second plane for application to the humerus. The distal plate portion has a bottom surface adapted for application to the surface of the humerus, and the distal plate portion has at least one overlapping hole formed therein. The osteotomy plate also includes a transition region connecting the proximal plate portion to the distal plate portion.

In another embodiment, the osteotomy plate includes a proximal plate portion lying substantially in a first plane for application to the humerus. The proximal plate portion has a bottom surface adapted for application to the surface of the humerus, and the proximal plate portion has at least one dynamic compression hole formed therein. The osteotomy plate also includes a distal plate portion lying substantially in a second plane for application to the humerus. The distal plate portion has a bottom surface adapted for application to the surface of the humerus, and the distal plate portion has at least one dynamic compression hole formed therein. The osteotomy plate also includes a transition region connecting the proximal plate portion to the distal plate portion, and a round non-dynamic compression hole located adjacent to the transition region and formed in either one or both of the proximal and the distal portions.

In one aspect, either one of the dynamic compression hole and the round hole is a threaded hole for engaging a bone screw having a thread configured and dimensioned to mate the thread of the threaded hole.

In one aspect, both of the dynamic compression hole and the round hole are threaded holes for engaging a bone screw having a thread configured and dimensioned to mate the thread of the threaded holes.

In another aspect, the osteotomy plate is a part of an osteotomy system which further includes a template for the osteotomy plate. The template includes an elongate member having a first end and second end: a first screw hole formed near the first end and a second screw hole formed near the second end, where the first and the second screw holes are positioned and dimensioned to accommodate the bone screws being used with the osteotomy plate. The template also has a gap formed near the center of the template, where the gap is dimensioned to accommodate the thickness of a saw blade being used to perform the osteotomy; and flare members formed on either side of the gap, where the flare members bridge the gap, so as not to impede the oscillation of a bone saw being used to perform the osteotomy.

For a further understanding of the nature and advantages of the invention, reference should be made to the following description taken in conjunction with the accompanying drawings.

BRIEF DESCRIPTION OF THE DRAWINGS

FIG. 1A is an exemplary top view diagram of a bone plate in accordance with a first embodiment of the present invention.

FIG. 1B is a cross-sectional view through section A-A of the plate of FIG. 1A.

FIGS. 1C-D are end views of the plate of FIG. 1A.

FIG. 2A is an exemplary top view diagram of a bone plate in accordance with a second embodiment of the present invention.

FIG. 2B is a cross-sectional view through section A-A of the plate of FIG. 2A.

FIGS. 2C-D are end views of the plate of FIG. 2A.

DETAILED DESCRIPTION OF THE INVENTION

Figure 3A:
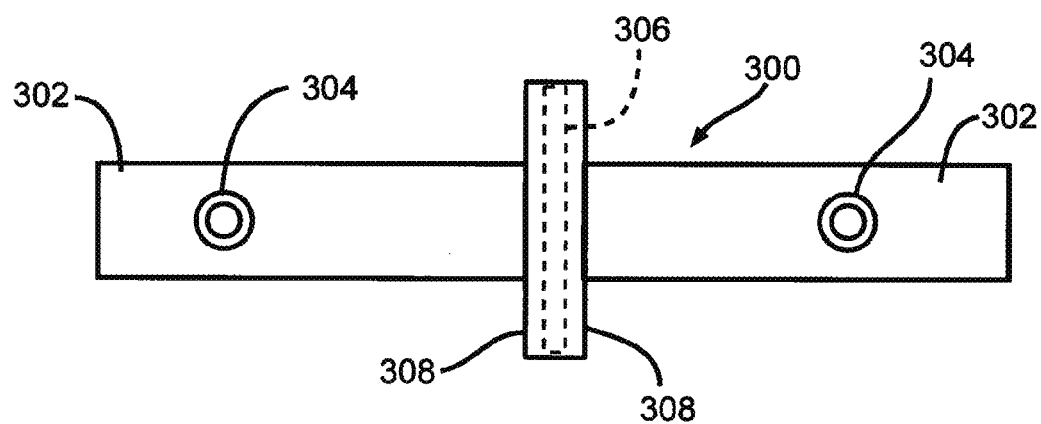
FIG. 3A is an exemplary top view diagram of a slide osteotomy template in accordance with the embodiments of the present invention.
Figure 3B:
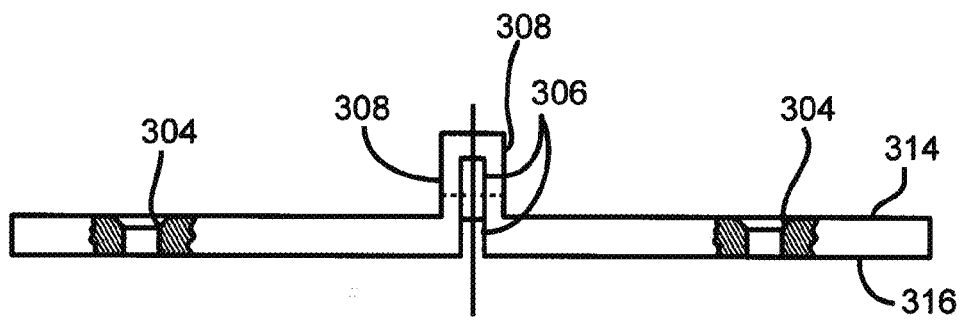
FIG. 3B is a front view of the template of the template of FIG. 3A.

The embodiments of the present invention are directed towards an osteotomy plate and a template for performing an osteotomy. The osteotomy plate as described herein is particularly applicable to a slide osteotomy operation, and more specifically it is adapted for a canine humeral osteotomy operation. It has been observed by the inventors herein that following 4 and 8 mm sliding osteotomies, mean forces on proximal articular surface of the ulna are reduced by approximately 25% and 28%, respectively. The proximal articular surface of the ulna contributes significantly to load transfer through the canine elbow joint. Abnormalities, which significantly increase this load, may contribute to canine elbow dysplasia, specifically fragmentation of the medial coronoid process and osteochondritis dissecans of the medial aspect of the humeral condyle. The overall reduction in mean joint surface force across the proximal articular surface of the ulna following humeral slide osteotomy indicates that this technique can provide a viable option in the clinical setting to reduce force transfer within the medial aspect of the elbow joint in cases of medial compartmental osteoarthritis of the canine elbow joint.

FIG. 1A is an exemplary top view diagram of a bone plate 100 in accordance with a first embodiment of the present invention. The plate 100 is a novel osteotomy plate having a plurality of holes for bone screws to hold the plate 100 against a bone. The holes 102 are of the dynamic compression type such that while the plate is connected to a bone via screws mounted through the holes 102, a compressive force is imparted to the bone sections which causes the bone sections to move towards the centerline 104 of the plate 100. The plate may be manufactured of stainless steel, titanium, or other nonreactive material. The plate 100 includes various novel features. A first novel feature is directed to the presence of a step or transition region 106 (shown better in FIG. 1B). The step or transition region 106 connects a first or proximal plate portion or region 108 to a second or distal plate portion or region 110. In this manner the transition region 106 offsets the proximal 108 and distal 110 portions of the plate. The degree of offset is variable and can range from approximately 2 mm to 16 mm, depending upon the degree of translation that is desired. A second novel feature is that one of the holes 112 which is closest to the transition 106 is a round (i.e., nondynamic compression) hole. The size of the hole 112 as well as holes 102 depends upon the size of bone screw being used to secure the plate to the bone. The round hole 112 is dimensioned to increase the distance between the bone screw and the osteotomy site. The increased distance decreases the stress riser effect and therefore decreases the risk of fracture between the screw hole and the osteotomy site. The decreased risk of fracture decreases the risk of surgical complications or failures.

FIGS. 1C-D are end views of the plate of FIG. 1A. FIGS. 1C-D show that the plate 100 has a top surface 114 and a bottom surface 116. The bottom surface 114 has a curved surface that is shaped for close application to the bone (e.g., humerus).

It should be realized that the width of the plate 100 is variable depending upon the size of the bone screw(s) which are to be used with the plate. Furthermore, the length of the plate is also variable depending upon the number of screws which are to be used with the plate.

FIG. 2A is an exemplary top view diagram of a bone plate 200 in accordance with a second embodiment of the present invention. Similar to the plate 100 of FIGS. 1A-D, the plate 200 is a novel osteotomy plate having a plurality of holes for bone screws to hold the plate 200 against a bone. The holes 202 are of the dynamic compression type such that when the plate is connected to a bone via screws mounted through the holes 202, a compressive force is imparted to the bone sections which causes the bone sections to move towards the centerline 204 of the plate 200. The plate may be manufactured of stainless steel, titanium, or other nonreactive material. The plate 200 includes various novel features. A first novel feature is directed to the presence of a step or transition region 206 (shown better in FIG. 2B). The step or transition region 206 connects a first or proximal plate portion or region 208 to a second or distal plate portion or region 210. In this manner the transition region 206 offsets the proximal 208 and distal 210 portions of the plate. The degree of offset is variable and can range from approximately 2 mm to 16 mm, depending upon the degree of translation that is desired. A second novel feature is that one of the holes 212 which is closest to the transition 206 is a round (i.e., nondynamic compression hole). While in FIGS. 2A and 1A, the round hole is shown on the distal portion, it should be realized that the round hole (212 or 112) may be formed adjacent to the step and in the proximal portion. The size of the hole 212 as well as holes 202 depend upon the size of bone screw being used to secure the plate to the bone. The round hole 212 increases the distance between the screw and the osteotomy site. The increased distance decreases the stress riser effect and therefore decreases the risk of fracture between the screw hole and the osteotomy site. The decreased risk of fracture decreases the risk of surgical complications or failures.

In addition to the novel features described above, another novel feature of plate 200 is that the one or more, or all of the holes 202 and 212 are threaded so as to accept locking screws. The locking-type bone screws thread into the plate 200 as well as the bone. The locking screw hole(s) are designed to work with different designs of locking screws. Conventional (e.g., nonlocking) bone screws are compressed against the plate 200 but do not lock or thread into the plate. Threading the bone screw into the bone plate as well as into the bone increases the stiffness of the construct (i.e., the combination of bone and implants). The increased stiffness increases the rate of bone healing and the decreases the risk of complications.

FIGS. 2C-D are end views of the plate of FIG. 2A. FIGS. 2C-D show that the plate 200 has a top surface 214 and a bottom surface 216. The bottom surface 216 has a curved profile that is shaped for close application to the bone (e.g., humerus).

It should be realized that the width of the plate 200 is variable depending upon the size of the bone screw (s) which are to be used with the plate. Furthermore, the length of the plate is also variable depending upon the number of screws which are to be used with the plate.

FIG. 3A is an exemplary top view diagram of a slide osteotomy template 300 in accordance with the embodiments of the present invention. The device 300 is a template configured to enable accurate alignment, screw placement, and osteotomy for use with the slide osteotomy plate of FIGS. 1A-D, FIGS. 2A-D, and FIGS. 4A-G, for example for the treatment of osteoarthritis. The novel features of the template 300 include its size, which is configured to match a given slide osteotomy plate, accurate drill hole locations for the osteotomy plate and accurate guidance for the osteotomy.

The device 300 includes a generally rectangular-shaped piece of stainless steel, titanium or other nonreactive material. The overall length of template 300 is configured to match the overall length of the osteotomy plate 100, 200 and 400. In general, the size of the template varies with the size of the corresponding osteotomy plate. Near either end 302 of the template 300 is a round hole 304 sized to accept a bone screw. The hole size varies depending upon the size of the bone screws being used (e.g., 2.7 mm, 3.5 mm, 4.5 mm, and so on). Near the center of the template is a transverse gap 306 in the template. The gap width varies depending upon the thickness of the saw blade being used to perform the osteotomy. The area of the template on either side of the gap 306 are connected by flares of material 308 that bridge the osteotomy gap 306 without impeding the oscillation of the bone saw. The gap between the flares 308 is approximately the same dimension as the gap as the base of the template. The gap 306 ensures that the osteotomy is performed approximately perpendicular to the bone plate and the bone.

The template 300 enables its user to pre-drill the bone to eliminate the risk of rotation of the osteomized bone segments. The position of the screw holes stabilizes the template while preparing bone holes that will enable dynamic compression when the corresponding slide osteotomy plate is applied to the bone. The flares 308 and the gap 306 near the center of the template ensure that the osteotomy is performed perpendicular to the bone plate and the bone. The resulting accurate osteotomy and compression increase the stability of the resulting composite structure (i.e., plate and screws) increasing the rate of healing and decreasing the risk of complication and failure. The accurate positioning of the screw holes reduces or eliminates the risk of rotational malalignment diminishing the risk of mal-union.

Figure 3C:
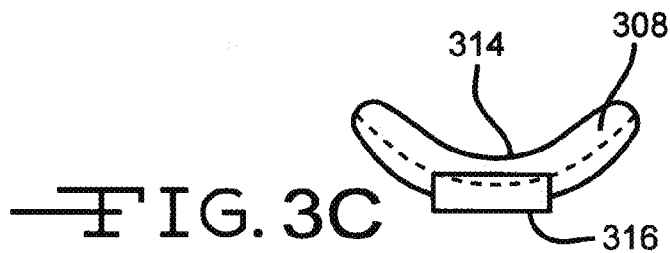
FIG. 3C is a side view of the template of the template of FIG. 3A.

FIG. 3C is a side view of the template of FIG. 3A. This figure (FIG. 3C) show that the plate template has a top surface 314 and a bottom surface 316. The bottom surface 316 has a curved profile that is shaped for close application to the bone (e.g., humerus).

Figure 4A:
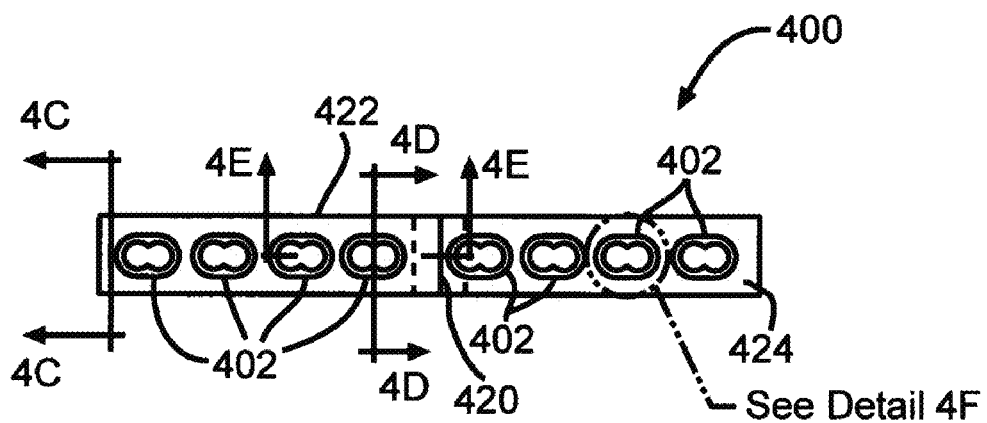
FIG. 4A is an exemplary top view diagram of a bone plate in accordance with a third embodiment of the present invention.
Figure 4B:
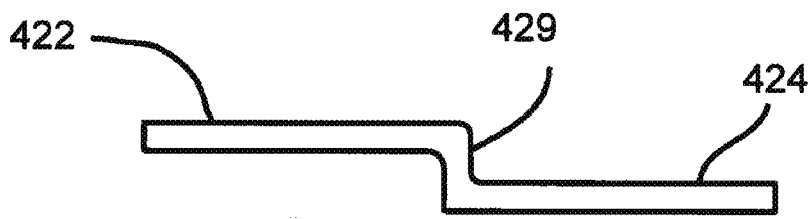
FIG. 4B is a side view diagram corresponding to the bone plate of FIG. 4A.
Figures 4C, 4D:
FIG. 4C is a cross-sectional view through section A-A of the bone plate of FIG. 4A.
FIG. 4D is a cross-sectional view through section B-B of the bone plate.

FIG. 4A is an exemplary top view diagram of a bone plate in accordance with a third embodiment of the present invention. A perspective view diagram corresponding to the bone plate of FIG. 4A is shown in FIG. 4G. As is shown in FIG. 4A, a bone plate 400 is a novel osteotomy plate having a plurality of overlapping holes 402 for bone screws to hold the plate 400 against a bone. The bone plate can be manufactured of stainless steel, titanium or other non-reactive materials of sufficient strength. The plate includes various novel features. A first novel feature is directed to the step 420 connecting a first plate portion 422 to a second plate portion 424. The step 420 offsets the first portion 422 and the second portion 424 of the plate 400. The degree of the step is variable and in one embodiment it is between 2 mm to 16 mm. The degree of offset is a variable depending upon the degree of translation that is desired. Another novel feature is that at least one of the holes 402 has threads for accepting a locking screw. It should be appreciated that any given hole is an overlapping type hole and it can be formed as a compression slot with the option of featuring a locking thread, or it could be a round hole featuring a locking thread. Furthermore, the threads can be tapered or rounded enabling it to mate with a matching screw head design. Alternatively, the plate can use the holes without using the locking feature.

The width of the bone plate is variable depending upon the size of the bone screws that are used with the plate. The length of the plate is also variable depending upon the number of screws that are used with the plate. The size of the hole 402 depends upon the size of bone screw being used to secure the plate to the bone.

Figure 4E:
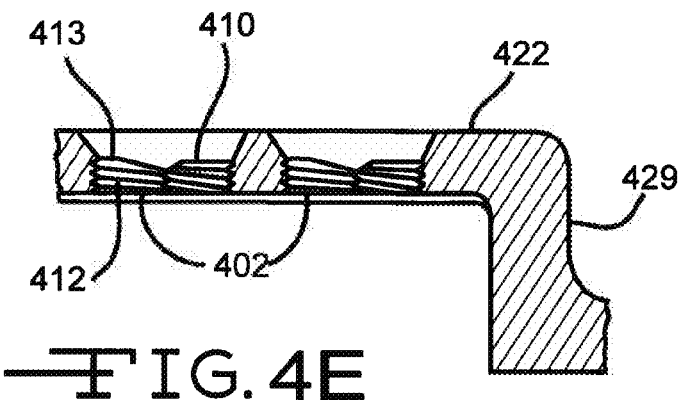
FIG. 4E is a cross-sectional view through section C-C of the bone plate of FIG. 4A.
Figure 4F:
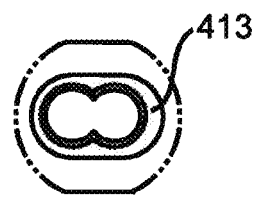
FIG. 4F shows detail view E corresponding to the bone plate of FIG. 4A of FIG. 4A.
Figure 4G:
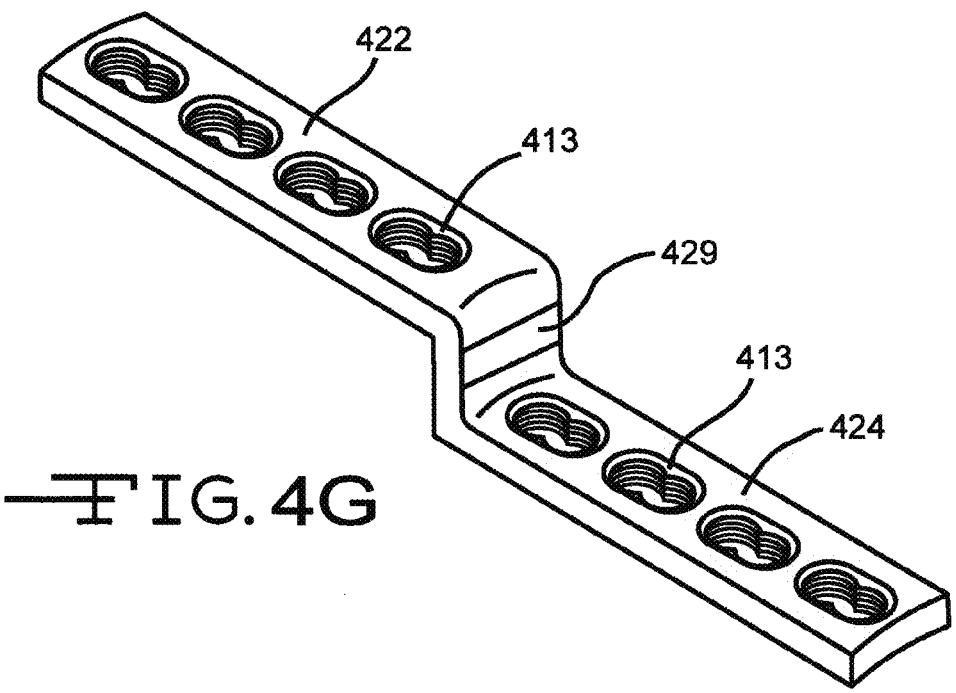
FIG. 4G is a perspective view diagram corresponding to the bone plate of FIG. 4A.

As is shown in FIG. 4E, the holes 402 have a round or oblong profile to act as compression type holes. For the overlapping holes, preferably, the compression holes 412 in the overlapping hole arrangement are the one farther away from the step 420, whereas the non-compression holes 410 are the ones nearer to the step 420. For the compression hole 412, a stepped surface 413 creates the compression effect as the bone plate is attached to the bone, such that while the plate is connected to a bone via screws mounted through the holes 412, a compressive force is imparted to the bone sections which causes the bone sections to move towards the centerline of the plate. In addition, the stepped surface 413 is also shown in FIG. 4F, and is shown to be farther away from the step 420.

The locking screw holes are designed to work with different designs of locking screws. Locking screws thread into the bone plate as well as into the bone. Threading the screws into the bone plate as well as into the bone increases the stiffness of the construct (i.e. the combination of bone and implants—(i.e., plate and screws). The increased stiffness increases the rate of bone healing and decreases the risk of complications.

Various other aspects of the overlapping holes 402 of plate 400 are described in further detail in International Patent Application No. PCT/IB2004/000911 and U.S. patent application Ser. No. 10/809,034, the disclosures of which are herein incorporated by reference in their entireties for all purposes, not inconsistent with the present application. These other aspects include details related to various alternative embodiments, describing: the number of overlapping holes (e.g., two or more) in a given hole: holes formed normal to the top side of the plate or formed at an angle to the top side of the plate; overlapping holes arranged along a longitudinal axis of the bone plate or staggered along the longitudinal axis: the degree of countersink: and kits having the stepped bone plate in combination with bone screws.

FIG. 4C is a cross-sectional view through section A-A of the bone plate of FIG. 4A. FIG. 4C shows that the plate 400 has a top surface 406 and a bottom surface 404. The bottom surface 404 has a curved surface that is shaped for close application to the bone (e.g., humerus).

FIG. 4D shows a cross-sectional view through section B-B of the bone plate of FIG. 4A.

As will be understood by those skilled in the art, other equivalent or alternative devices and templates for performing a slide osteotomy according to the embodiments of the present invention can be envisioned without departing from the essential characteristics thereof. For example, the osteotomy plate or the template may be made in various sizes depending on the size of the bone and the desired osteotomy procedure. Furthermore, the osteotomy plate may have any number of threaded or nonthreaded dynamic compression, noncompression-type, or overlapping holes. Accordingly, the foregoing disclosure is intended to be illustrative, but not limiting, of the scope of the invention which is set forth in the following claims.

What is claimed is:

1. A bone plate, comprising:
  a) a proximal plate portion lying substantially in a first plane, the proximal plate portion having a proximal plate thickness extending from a top proximal plate surface to a bottom proximal plate surface with at least one threaded hole formed through the proximal plate thickness;
  b) a distal plate portion lying substantially in a second plane, the distal plate portion having a distal plate thickness extending from a top distal plate surface to a bottom distal plate surface with at least one threaded hole formed through the distal plate thickness;
  c) a transition region, connecting the proximal plate portion lying in the first plane to the distal plate portion lying in the second plane, wherein the first plane is substantially parallel to the second plane; and
  d) wherein at least one of the threaded holes in either the proximal plate portion or the distal plate portion is an overlapping threaded hole comprising an unthreaded upper portion extending from an oval shaped opening at either the top proximal plate surface or the top distal plate surface part way through the respective thickness thereof to a threaded lower portion having an hourglass shape extending from where the upper portion ends at the hourglass shape to the bottom proximal plate surface or the bottom distal plate surface with threaded surfaces of the overlapping holes meeting each other at a threaded overlap forming the hourglass shape, the threaded lower portion being adapted to lock with threads of a corresponding bone screw in either one or the other of the overlapping holes.

2. The bone plate of claim 1 wherein the transition region is a stepped transition region which is substantially nonparallel to either of the first plane or the second plane.

3. The bone plate of claim 1 wherein the plate is of a material selected from the group consisting of stainless steel, titanium, a nonreactive material, and combinations thereof.

4. The bone plate of claim 1 wherein the overlapping threaded hole in at least one of the proximal plate portion or the distal plate portion is formed normal to the respective top proximal plate surface or the top distal plate surface, as the case may be.

5. The bone plate of claim 1 wherein the overlapping threaded hole in at least one of the proximal plate portion or the distal plate portion is formed at an angle offset from normal to the respective top proximal plate surface or the top distal plate surface, as the case may be.

6. The bone plate of claim 1 wherein a first of the overlapping threaded holes is formed normal to either the top proximal plate surface or the top distal plate surface and a second of the overlapping threaded holes is formed at an angle offset from normal to the other of the top proximal plate surface or the top distal plate surface.

7. The bone plate of claim 1 wherein the overlapping threaded hole in at least one of the proximal plate portion and the distal plate portion is one of a set of overlapping holes.

8. The bone plate of claim 7 wherein the set of overlapping holes are aligned along a longitudinal axis of the plate.

9. The bone plate of claim 7 wherein the set of overlapping holes are positioned in a staggered arrangement with respect to a longitudinal axis of the plate.

10. The bone plate of claim 1 as part of a kit including a template, the template comprising:
  a) an elongate member having a first end and a second end;
  b) a first screw hole formed near the first end and a second screw hole formed near the second end, the first and second screw holes being positioned and dimensioned to accommodate bone screws;
  c) a gap formed near a center of the template, the gap dimensioned to accommodate a saw blade; and
  d) flare members formed on either side of the gap, the flare members bridging the gap so as not to impede oscillation of the bone saw.

11. The template of claim 10 wherein the template is of a material selected from the group consisting of stainless steel, titanium, a nonreactive material, and combinations thereof.

12. The bone plate of claim 1 wherein the upper portion of the overlapping threaded hole comprises a compression ramp extending from the oval shaped opening at the top proximal plate surface or the top distal plate surface downwardly and inwardly part way through the respective thickness thereof to the threaded lower portion.

13. A bone plate, comprising:
  a) a proximal plate portion lying substantially in a first plane, the proximal plate portion having a proximal plate thickness extending from a top proximal plate surface to a bottom proximal plate surface with at least one threaded hole formed through the proximal plate thickness;
  b) a distal plate portion lying substantially in a second plane, the distal plate portion having a distal plate thickness extending from a top distal plate surface to a bottom distal plate surface with at least one threaded hole formed through the distal plate thickness;
  c) a transition region connecting the proximal plate portion lying in the first plane to the distal plate portion lying in the second plane, wherein the first plane is substantially parallel to the second plane;
  d) wherein at least one of the threaded holes in either the proximal plate portion or the distal plate portion is an overlapping threaded hole comprising an unthreaded upper portion extending from an oval shaped opening at either the top proximal plate surface or the top distal plate surface part way through the respective thickness thereof to a threaded lower portion having an hourglass shape extending from where the upper portion ends at the hourglass shape to the bottom proximal plate surface or the bottom distal plate surface with threaded surfaces of the overlapping holes meeting each other at a threaded overlap forming the hourglass shape, the threaded lower portion being adapted to lock with threads of a corresponding bone screw in either one or the other of the overlapping holes; and e) a round hole without a compression ramp located adjacent to the transition region and formed in at least one of the proximal plate portion and the distal plate portion.

14. The bone plate of claim 13 wherein the transition region is a stepped transition region which is substantially nonparallel to either of the first plane or the second plane.

15. The bone plate of claim 13 wherein the plate is of a material selected from the group consisting of stainless steel, titanium, a nonreactive material, and combinations thereof.

16. The bone plate of claim 13 as part of a kit further comprising a template, the template comprising:

a) an elongate member having a first end and a second end;

b) a first screw hole formed near the first end and a second screw hole formed near the second end, the first and second screw holes being positioned and dimensioned to accommodate bone screws used with the bone plate;

c) a gap formed near the center of the template, the gap dimensioned to accommodate a saw blade; and d) flare members formed on either side of the gap, the flare members bridging the gap so as not to impede oscillation of the bone saw.

17. The bone plate of claim 13 wherein the upper portion of the overlapping threaded hole comprises a compression ramp extending from the oval shaped opening at the top proximal plate surface or the top distal plate surface downwardly and inwardly part way through the respective thickness thereof to the threaded lower portion.

18. The bone plate of claim 13 wherein the overlapping threaded hole in at least one of the proximal plate portion or the distal plate portion is formed normal to the respective top proximal plate surface or the top distal plate surface, as the case may be.

19. The bone plate of claim 13 wherein the overlapping threaded hole in at least one of the proximal plate portion or the distal plate portion is formed at an angle offset from normal to the respective top proximal plate surface or the top distal plate surface, as the case may be.

20. The bone plate of claim 13 wherein the overlapping threaded hole in at least one of the proximal plate portion and the distal plate portion is one of a set of overlapping holes.

* * * * *